US 11,007,335 B2

(12) United States Patent
McCracken (10) Patent No.: US 11,007,335 B2
(45) Date of Patent: May 18, 2021

(54) NON-INVASIVE VENTILATION BRONCHOSCOPY SCOPE GUIDE AND METHOD (71) Applicant: KONINKLIJKE PHILIPS N.V., Eindhoven (NL)

(72) Inventor: Christopher James McCracken, Harrison City, PA (US)

(73) Assignee: Koninklijke Philips N.V., Eindhoven (NL)

(*) Notice: Subject to any disclaimer, the term of this patent is extended or adjusted under 35 U.S.C. 154(b) by 382 days.

(21) Appl. No.: 15/746,028

(22) PCT Filed: Jul. 4, 2016

(86) PCT No.: PCT/IB2016/053996
§ 371 (c)(1),
(2) Date: Jan. 19, 2018

(87) PCT Pub. No.: WO2017/013515
PCT Pub. Date: Jan. 26, 2014

(65) Prior Publication Data
US 2018/0214651 A1    Aug. 2, 2018

Related U.S. Application Data (60) Provisional application No. 62/195,360, filed on Jul. 22, 2015.

(51) Int. Cl.
A61M 16/04    (2006.01)
A61B 1/00    (2006.01)
(Continued)

(52) U.S. Cl.
CPC ..... A61M 16/0488 (2013.01); A61B 1/00154 (2013.01); A61B 1/01 (2013.01);
(Continued)

(58) Field of Classification Search
CPC .............. A61M 16/04; A61M 16/0402; A61M 16/0463; A61M 16/0488–0497;
(Continued)

(56) References Cited

U.S. PATENT DOCUMENTS 3,815,596 A    6/1974 Keener et al.
3,905,361 A *  9/1975 Hewson ............ A61M 16/0484
                                                    128/202.16
(Continued)

FOREIGN PATENT DOCUMENTS

| WO | 0154859 A | 4/2001 |
| WO | 2011086432 A2 | 7/2011 |
| WO | 2012100016 A1 | 7/2012 |

OTHER PUBLICATIONS

Esquinas et al: "Bronchoscopy During Non-Invasive Mechanical Ventilation: A Review of Techniques and Procedures"; Arch Bronconeumol. 2013: 49(3), pp. 105-112.

Primary Examiner — Kendra D Carter
Assistant Examiner — Elliot S Ruddie
(74) Attorney, Agent, or Firm — Daniel H. Brean (57) ABSTRACT A bronchoscopy scope guide (30) for a non-invasive ventilation (NIV) patient interface (10) comprises a semi-rigid scope guide tube (32), a bronchoscopy scope seal (48), and a semi-rigid grommet (34). The semi-rigid scope guide tube (32) includes a principal axis (36) and entrance and exit guide portions (38,40). The bronchoscopy scope seal (48) couples to the scope guide tube for sealing around a bronchoscopy scope when inserted through the scope guide tube. The semi-rigid grommet (34) is disposed about an outer circumference of and flexibly coupled to the scope guide tube (32) and is located in a principal plane (52) transverse to the principal axis of the scope guide tube. The scope guide tube (32) is pivotally manipulate-able about the flexible coupling of the grommet (34) for positioning a distal end (Continued)

(46) of the exit guide portion of the scope guide tube proximate, but not in contact with, one of a nasal cavity or mouth opening of a patient for assisted guidance control of the bronchoscopy scope within an interior region (58) of the patient interface (10) in performance of a bronchoscopy procedure.

22 Claims, 6 Drawing Sheets (51) Int. Cl.
*A61B 1/01* (2006.01)
*A61M 16/06* (2006.01)
*A61M 16/08* (2006.01)
*A61B 1/267* (2006.01)

(52) U.S. Cl.
CPC ............ *A61B 1/267* (2013.01); *A61B 1/2676* (2013.01); *A61M 16/06* (2013.01); *A61M 16/0683* (2013.01); *A61M 16/0816* (2013.01); *A61M 16/0627* (2014.02); *A61M 16/0633* (2014.02); *A61M 2210/005* (2013.01); *A61M 2210/0618* (2013.01); *A61M 2210/0625* (2013.01); *A61M 2210/1035* (2013.01)

(58) Field of Classification Search
CPC .... A61M 16/06–0655; A61M 16/0683; A61M 16/0078; A61M 16/08–0855; A61M 16/208; A61M 2210/005; A61M 2210/0618; A61M 2210/0625; A61M 2210/1025–1039; A61M 16/0627; A61M 16/0633; A61M 16/20; A61B 1/2676; A61B 1/01–0125; A61B 1/018; A61B 1/00147–00154; A61B 1/00165; A61B 1/267; A61B 1/005; A61B 1/008
USPC ................ 128/207.11, 206.28; 600/114, 14, 600/153–153, 156, 158–159
See application file for complete search history.

(56) References Cited

U.S. PATENT DOCUMENTS

| | | |
|---|---|---|
| 4,041,936 A | 8/1977 | Carden |
| 5,694,929 A | 12/1997 | Christopher |
| 6,631,713 B1 * | 10/2003 | Christopher ...... A61M 16/0488 128/200.21 |
| 6,895,966 B2 * | 5/2005 | Christopher ...... A61M 16/0488 128/200.26 |
| 7,473,219 B1 | 1/2009 | Glenn |
| 9,038,968 B2 * | 5/2015 | Hennon ................ F16L 3/1091 248/65 |
| 2006/0249160 A1 * | 11/2006 | Scarberry ............ A61B 5/0836 128/207.13 |
| 2013/0296653 A1 * | 11/2013 | Brown ............... A61B 1/00154 600/114 |
| 2014/0275772 A1 * | 9/2014 | Chuda ............... A61M 16/0418 600/104 |

* cited by examiner

NON-INVASIVE VENTILATION BRONCHOSCOPY SCOPE GUIDE AND METHOD

CROSS-REFERENCE TO PRIOR APPLICATIONS

This application is the U.S. National Phase application under 35 U.S.C. § 371 of International Application No. PCT/IB2016/053996, filed on Jul. 4, 2016, which claims the benefit of U.S. Provisional Patent Application No. 62/195,360, filed on Jul. 22, 2015. These applications are hereby incorporated by reference herein.

The present embodiments relate generally to bronchoscopy and non-invasive ventilation patient interfaces and more particularly, to a non-invasive ventilation bronchoscopy scope guide and method.

Bronchoscopy is a common procedure used to visually inspect the bronchial tree of a patient. Flexible Bronchoscopy is an endoscopic procedure that involves feeding a tubular fiberoptic scope through either the mouth or nose of the patient to reach the desired location for inspection.

While the diameter of the scope is generally small when compared to the size of the patient airway, there is a risk of maintaining adequate ventilation to some patients during the procedure, especially to those patients who are receiving positive pressure ventilation (PPV). However, one disadvantage of bronchoscopy is that the bronchoscopy scope can significantly increase the resistance to flow in the airway, causing the patient discomfort or respiratory distress.

Figure 1:
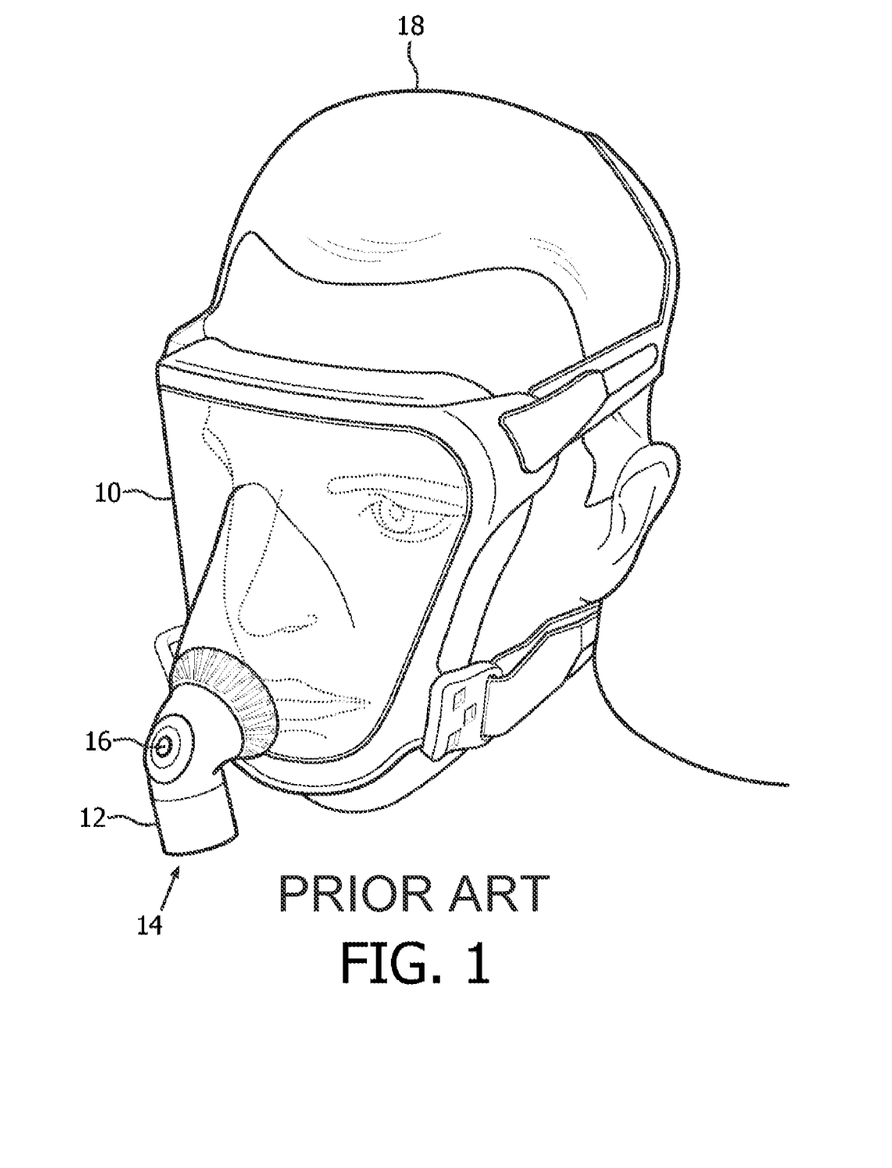
FIG. 1 is a perspective view of a non-invasive ventilation mask known in the art.

To avoid this issue, a number of commercially available masks or adapters have been developed that allow performance of a bronchoscopy procedure through a non-invasive ventilation (NIV), or non-invasive positive pressure ventilation (NPPV), mask. FIG. 1 is a perspective view of a non-invasive ventilation mask 10 known in the art. The masks, or mask adapters, e.g., elbow/adapter 12, typically contain a connection, i.e., a ventilator circuit connection port 14, for a breathing circuit to allow the mask or adapter to be coupled to a positive pressure ventilator (not shown). The mask or adapter also includes a port 16 which allows feeding of a flexible bronchoscopy scope (see FIG. 2, flexible bronchoscopy scope 20) through the mask to the nasal or mouth opening of a patient 18 receiving the bronchoscopy procedure. In most cases, the port 16 contains some form of seal, or sealing diaphragm, for sealing around the bronchoscopy tubular fiberoptic scope to maintain positive pressure in the mask.

When the bronchoscopy procedure is performed on a patient not receiving NIV/NPPV, the physician performing the procedure generally holds the body of the scope in one hand, while guiding the flexible fiberoptic tube into the airway. The guiding hand is generally placed at the entrance of the nose or mouth, to gain the greatest leverage in guiding the scope during the bronchoscopy procedure.

Figure 2:
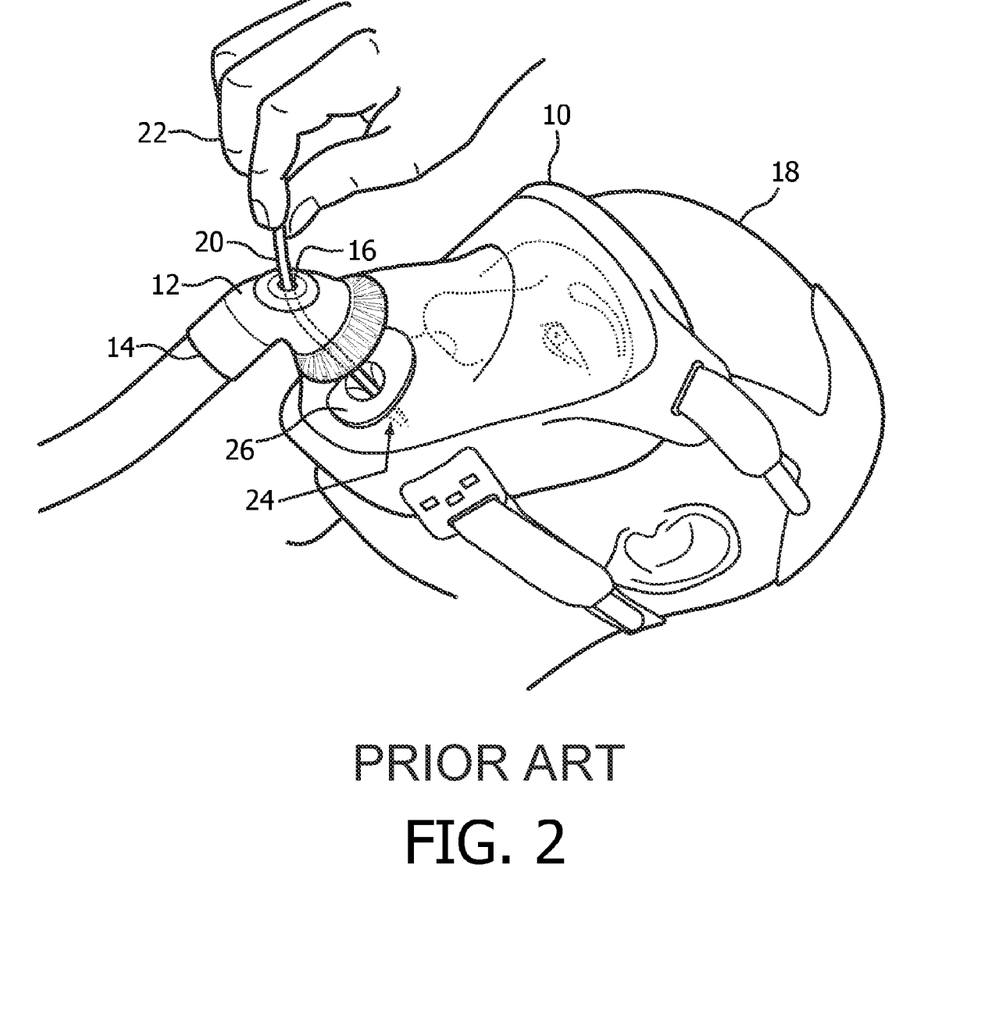
FIG. 2 is a perspective view of a physician performing a bronchoscopy procedure on a patient through a non-invasive ventilation mask and mask adapter known in the art.

When the same procedure is performed through a mask or mask adapter, the physician's guiding hand can no longer be placed proximal to the nose or mouth, due to the presence of the mask or adapter. The guiding hand is thus placed at the entrance to the bronchoscopy port in the mask or adapter, which can be approximately two to three inches (2-3 inches) away from the desired nasal or mouth opening. FIG. 2 illustrates a perspective view of one example of a physician performing a bronchoscopy procedure on a patient 18 through a non-invasive ventilation mask 10 and mask adapter 12 as is known in the art.

From the illustration of FIG. 2, one can see that the physician's guiding hand 22 is distant from the mouth opening 24, which can be problematic for insertion of the scope 20 through the mask 10 and adapter 12 and into the mouth 24. That is, the difference in location of the guiding hand 22 can make it more difficult to perform the bronchoscopy procedure as the scope 20 can bend or loop inside the mask 10, making it difficult to feed through the patient's airway. FIG. 2 also illustrates the use of a mouthpiece 26 for keeping a patient's mouth open; however, the mouthpiece does nothing to mitigate the problem of bending and looping of the scope 20 inside the mask 10 and adapter 12.

Accordingly, an improved method and apparatus for overcoming the problems in the art is desired.

In accordance with one aspect, a non-invasive ventilation bronchoscopy scope guide provides a method to guide a bronchoscopy scope to at least one of a nasal or mouth opening for advantageously preventing an undesirable bending or looping of the bronchoscopy scope tube during a bronchoscopy procedure, especially during insertion.

According to one aspect, a bronchoscopy scope guide for a non-invasive ventilation (NIV) patient interface comprises a semi-rigid scope guide tube, a bronchoscopy scope seal, and a semi-rigid grommet. The semi-rigid scope guide tube includes a principal axis along a length dimension thereof, further having an entrance (input) guide portion and an exit (output) guide portion. The bronchoscopy scope seal couples to the scope guide tube for sealing between the scope guide tube and around a bronchoscopy scope, in response to the bronchoscopy scope being inserted through the scope guide tube. The bronchoscopy scope seal further enables maintaining of a positive pressure within the patient interface during usage of the patient interface for non-invasive ventilation. The semi-rigid grommet is disposed about an outer circumference of and flexibly coupled to the scope guide tube via a flexible intermediate region. The grommet is also located in a principal plane transverse to the principal axis of the scope guide tube, in-between the entrance and exit guide portions thereof.

The scope guide tube is pivotally manipulate-able about the flexible coupling of the grommet for positioning a distal end of the exit guide portion of the scope guide tube proximate, but not in contact with, one of a nasal cavity or mouth opening of a patient. The bronchoscopy scope guide thus provides for assisted guidance control of the bronchoscopy scope within an interior region of the patient interface that extends from at least an interior surface of the patient interface to the patient's face. The bronchoscopy scope guide also prevents undesirable bending or looping of the bronchoscopy scope within the interior region of the patient interface during insertion of the bronchoscopy scope into the nasal cavity or mouth opening and associated airway of the patient in performance of a bronchoscopy procedure.

According to another aspect of the bronchoscopy scope guide, a length of the exit guide portion of the scope guide tube comprises a length sufficient to enable a desired pivotal movement of the exit guide portion within the interior region of the patient interface, but not a length insertable into the nasal or mouth opening and associated airway of the patient.

In another aspect of the bronchoscopy scope guide, the grommet is further configured for being secured to a port of the NIV patient interface, wherein the scope guide tube is flexibly held via the grommet to the port of the NIV patient interface, enabling the distal end of the exit guide portion to be pivotally moved around and positioned proximate, but not in contact with, one of at least the nasal cavity or the mouth opening of the patient. Additionally, the grommet can be secured to the port via at least one of an elbow and an adapter. According to yet another aspect of the bronchoscopy scope guide, the grommet can be secured to the port of the NIV patient interface via one of permanently secured or removably secured.

In a further aspect, the scope guide tube and grommet form an integral component part. The integral component part can also comprise the bronchoscopy scope seal. In another aspect of the bronchoscopy scope guide, the scope guide tube and grommet comprise a hard durometer silicone.

Still further, in another aspect, the bronchoscopy scope guide further comprises an NIV patient interface, wherein the NIV patient interface comprises one selected from the group consisting of a nasal mask, an oral-nasal face mask, and a helmet. The NIV patient interface can also comprise a non-invasive positive pressure ventilation (NPPV) mask.

In one aspect of the bronchoscopy scope guide, the grommet is removably secured to the NIV patient interface, and wherein the scope guide tube further comprises a reversible tube in which the exit guide portion can be used as the entrance guide portion and vise versa. In another aspect, the entrance guide portion comprises a straight section along the principal axis of the scope guide tube and the exit guide portion comprises both a straight section along the principal axis and a curved section away from the principal axis of the scope guide tube. In one embodiment, the curved section of exit guide portion is located at a distal end thereof. In another embodiment, the entrance guide portion is straight along the principal axis and the exit guide portion includes a section that curves away from the principal axis.

According to a further aspect of the bronchoscopy scope guide, the bronchoscopy scope seal couples to the scope guide tube at one selected from the group consisting of (i) at a proximal end of the entrance guide portion or a distal end of the exit guide portion, and (ii) at a position within the entrance guide portion or the exit guide portion, or at an intersection of the entrance guide portion and the exit guide portion. In one embodiment, the bronchoscopy scope seal is located within the scope guide tube at a location of the grommet.

According to another embodiment, a method of guiding a bronchoscopy scope for a non-invasive ventilation (NIV) patient interface, comprises: providing (i) a semi-rigid scope guide tube having a principal axis along a length dimension thereof, further having an entrance (input) guide portion and an exit (output) guide portion and (ii) a semi-rigid grommet being disposed about an outer circumference of and flexibly coupled to the scope guide tube via a flexible intermediate region and located in a principal plane transverse to the principal axis of the scope guide tube, in-between the entrance and exit guide portions thereof; sealing between the scope guide tube and around a bronchoscopy scope, via a bronchoscopy scope seal coupled to the scope guide tube, in response to the bronchoscopy scope being inserted through the scope guide tube, further enabling maintaining of a positive pressure within the patient interface during usage of the patient interface for non-invasive ventilation; and pivotally manipulating the scope guide tube about the flexible coupling of the grommet for positioning a distal end of the exit guide portion of the scope guide tube proximate, but not in contact with, one of a nasal cavity or mouth opening of a patient for assisted guidance control of the bronchoscopy scope within an interior region of the patient interface that extends from at least an interior surface of the patient interface to the patient's face, and for preventing undesirable bending or looping of the bronchoscopy scope within the interior region of the patient interface during insertion of the bronchoscopy scope into the nasal cavity or mouth opening and associated airway of the patient in performance of a bronchoscopy procedure.

In another embodiment, the method further comprises: securing the grommet to the NIV patient interface via at least one of directly to a port of the NIV patient interface, indirectly via an elbow coupled to the port, and indirectly via an adapter coupled to the port, wherein the scope guide tube is flexibly held via the grommet to the port of the NIV patient interface, enabling the distal end of the exit guide portion to be pivotally moved around and positioned proximate, but not in contact with, one of at least the nasal cavity or the mouth opening of the patient. In one aspect, the grommet is secured to the port of the NIV patient interface via one of permanently secured or removably secured. In another aspect, the grommet is removably secured to the NIV patient interface, and wherein the scope guide tube further comprises a reversible tube in which the exit guide portion can be used as the entrance guide portion and vise versa.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to the embodiments as discussed herein, a bronchoscopy scope guide comprises a hard durometer silicone, or other semi-rigid material. The scope guide further comprises a semi-rigid grommet to hold the guide to an elbow/adapter/mask of a non-invasive ventilations patient interface, and a flexible region that allows the scope guide to be moved around to position it at the nasal/mouth opening (e.g., in a manner similar to that of using a joystick) of a patient. The semi-rigid scope guide is configured to advantageously guide a bronchoscopy scope to the correct location. In addition, the scope guide can be inserted in the opening of an elbow/adapter, or be inserted directly into an opening on the mask. In another embodiment, the scope guide can be permanently fixed to the elbow/adapter/mask or be removable. In a further embodiment, for entering the nasal cavity, the end of the scope guide can be curved, as illustrated, to advantageously help guide the scope up into the nasal opening. In a still further embodiment, the scope guide could be reversible (e.g., the curved portion on the exterior of the elbow/adapter, for a mouth scope insertion), further as discussed herein.

Figure 3:
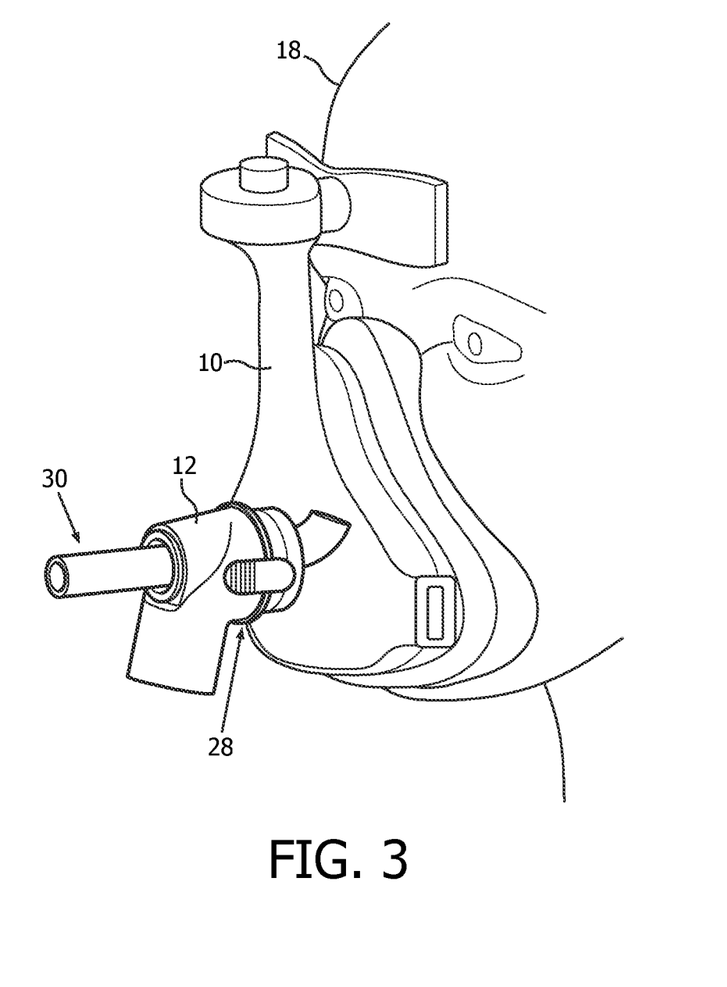
FIG. 3 is a perspective view of a bronchoscopy scope guide for a non-invasive ventilation (NIV) patient interface according to an embodiment of the present disclosure.

Turning now to FIG. 3, there is shown a perspective view of a bronchoscopy scope guide 30 for a non-invasive ventilation (NIV) patient interface 10 according to an embodiment of the present disclosure. The scope guide 30 is shown inserted in the opening of an elbow/adapter 12. The scope guide 30 could also be inserted directly into an opening 28 on the mask 10, e.g., at a location where the elbow/adapter 12 couples to the mask, with suitable modifications for a proper connection, as may be necessary, to one or both of the opening for receiving the scope guide and the scope guide.

Figure 4:
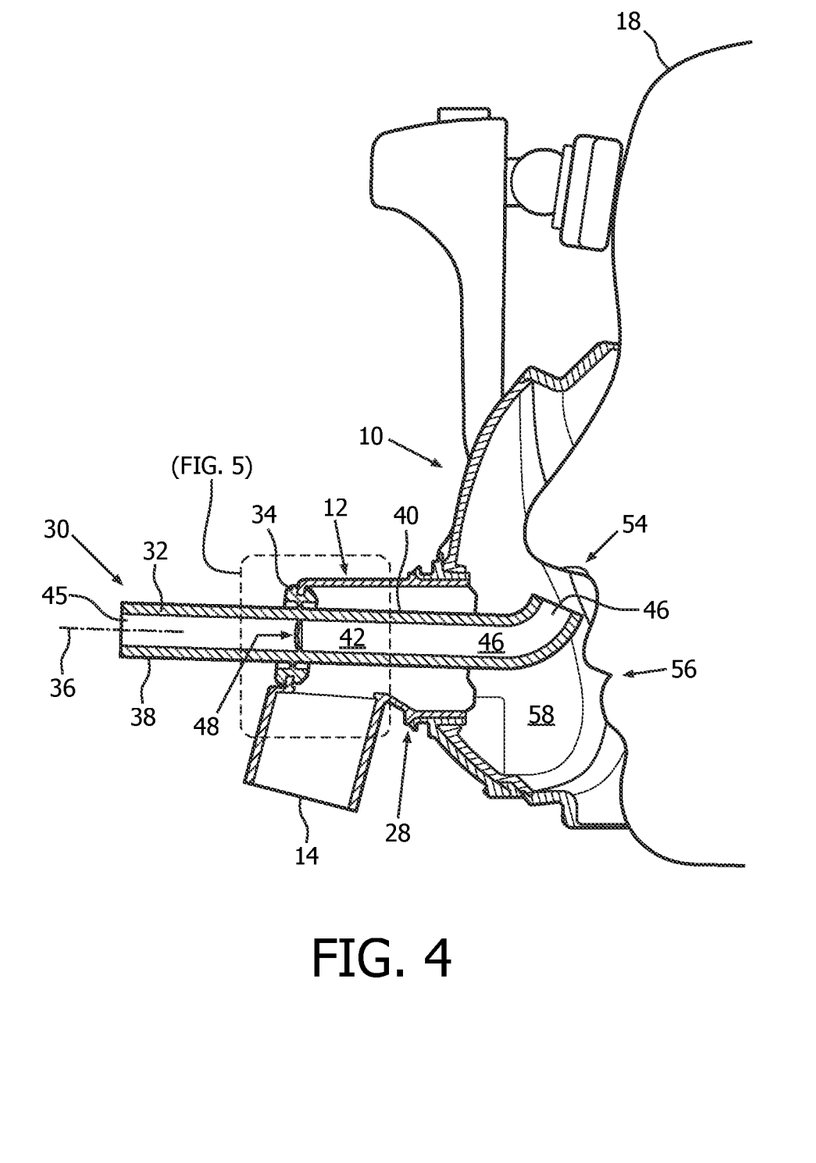
FIG. 4 is a sectional view along a length dimension of the bronchoscopy scope guide for a non-invasive ventilation (NIV) patient interface of FIG. 3 according to an embodiment of the present disclosure.
Figure 5:
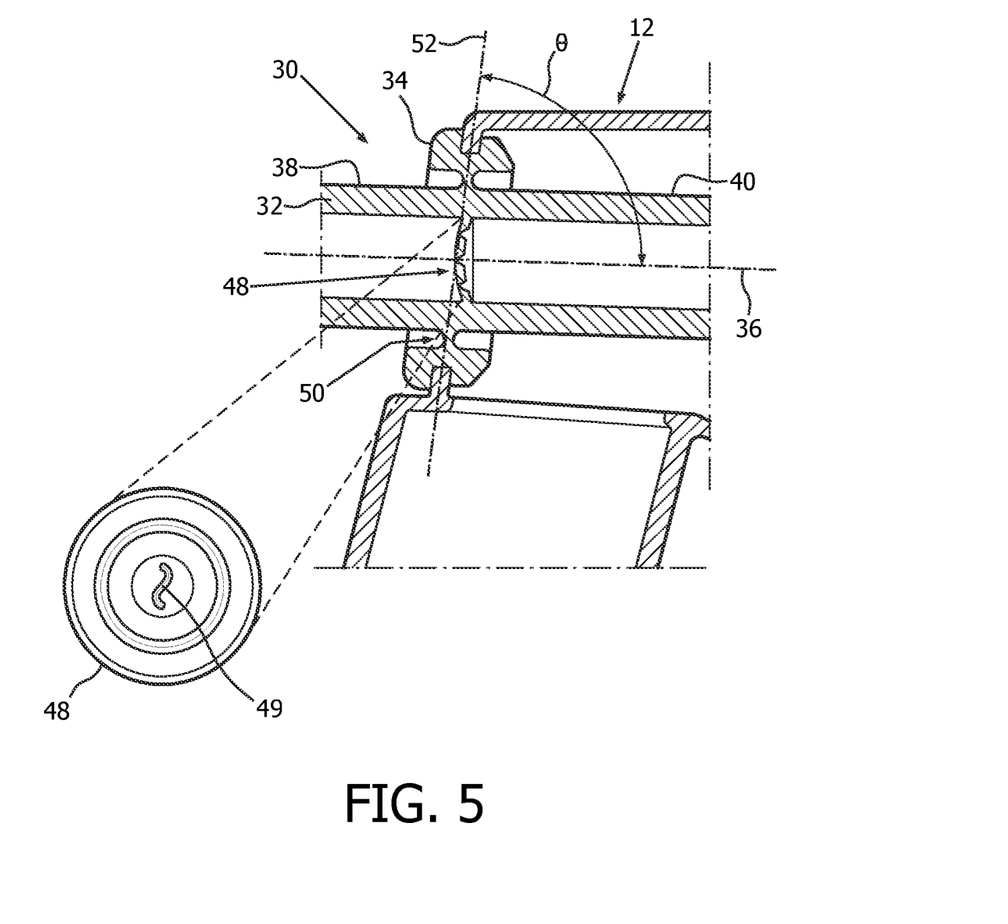
FIG. 5 is a portion of the sectional view along a length dimension of the bronchoscopy scope guide for a non-invasive ventilation (NIV) patient interface, indicated via a dashed-line box in FIG. 4, enlarged to show greater detail according to an embodiment of the present disclosure.

With reference now to FIGS. 4 and 5, a bronchoscopy scope guide 30 for a non-invasive ventilation (NIV) patient interface 10 comprises a semi-rigid scope guide tube 32 and a semi-rigid grommet 34. The semi-rigid scope guide tube 32 includes a principal axis 36 along a length dimension thereof, further having an entrance (input) guide portion 38 and an exit (output) guide portion 40. In one embodiment, the entrance guide portion 38 comprises a straight section along the principal axis 36 of the scope guide tube 32. In addition, the exit guide portion 40 comprises both a straight section 42 along the principal axis 36 and a curved section 44 away from the principal axis of the scope guide tube. For example, the curved section 44 of exit guide portion 40 is located at a distal end thereof, indicated by reference numeral 46. In another embodiment, the entrance guide portion 38 is straight along the principal axis and the exit guide portion 40 includes a section that curves away from the principal axis.

Referring still to FIGS. 4 and 5, a bronchoscopy scope seal 48 couples to the scope guide tube 32 for sealing between the scope guide tube 32 and around a bronchoscopy scope (not shown), in response to the bronchoscopy scope being inserted through the scope guide tube 32. The scope seal is generally flexible to adjust to the different sizes of scopes. When in use, the scope seal seals around the perimeter of the scope to maintain positive pressure inside the mask. A center region of the scope seal includes a small slit, e.g., an "S" shaped slit 49 or a slit of another suitable shape. The slit allows passage through of the bronchoscopy scope and seals around the scope perimeter. In addition, the slit is small enough, that it generally seals, with minimal air leakage, prior to scope insertion and after scope removal. The bronchoscopy scope seal 48 thus enables a maintaining of a positive pressure within the patient interface 10 during usage of the patient interface for non-invasive ventilation. In one embodiment, the bronchoscopy scope seal 48 couples to the scope guide tube 32 at one selected from the group consisting of (i) at a proximal end 45 of the entrance guide portion 38 or a distal end 46 of the exit guide portion 40, and (ii) at a position within the entrance guide portion 38 or the exit guide portion 40, or at an intersection of the entrance guide portion 38 and the exit guide portion 40. In a further embodiment, the bronchoscopy scope seal 48 is located within the scope guide tube 32 at a location of the grommet 34, as is shown in FIGS. 4 and 5.

As illustrated in FIGS. 4 and 5, the semi-rigid grommet 34 is disposed about an outer circumference of and flexibly coupled to the scope guide tube 32, for example, via a flexible intermediate region 50 of the semi-rigid grommet 34. In addition, the coupling between the semi-rigid grommet 34 and the scope guide tube 32 is permanent. Furthermore, the semi-rigid grommet 34 is located in a principal plane 52 transverse to the principal axis 36 of the scope guide tube 32, in-between the entrance and exit guide portions (38 and 40, respectively) thereof. For example, the principal plane 52 of the semi-rigid grommet 34 could be perpendicular to the principal axis 36 of the scope guide tube 32, or at a default orientation angle θ configured according to the particular requirements of a given NIV patient interface and bronchoscopy procedure/application.

In operation, the scope guide tube 32 is pivotally manipulate-able about the flexible intermediate region 50 of the grommet 34 for positioning a distal end 46 of the exit guide portion 40 of the scope guide tube 32 proximate, but not in contact with, one of a nasal cavity 54 or mouth opening 56 of a patient 18 (see FIG. 4). As a result, the bronchoscopy scope guide 30 advantageously provides for assisted guidance control of the bronchoscopy scope (not shown) within an interior region 58 of the patient interface 10 that extends from at least an interior surface of the patient interface to the patient's face, and for preventing undesirable bending or looping of the bronchoscopy scope (not shown) within the interior region 58 of the patient interface 10 during insertion of the bronchoscopy scope into the nasal cavity or mouth opening and associated airway of the patient in performance of a bronchoscopy procedure.

According to one embodiment of the bronchoscopy scope guide 30, the length of the exit guide portion 40 of the scope guide tube 32 comprises a length sufficient to enable a desired pivotal movement of the exit guide portion within the interior region 58 of the patient interface 10, but not a length insertable into the nasal or mouth opening and associated airway of the patient. In one embodiment, the exit guide portion 40 of the scope guide tube 32 extends at least 75% of a straight path distance from the elbow/adapter/mask to the nasal or mouth opening of a patient. In another embodiment, the length of the exit guide portion and a magnitude of its extension within a mask could vary depending on the style of mask used, so long as the amount of un-guided scope distance within the interior region of the mask is reduced as much as possible.

With reference still to FIGS. 4 and 5, the grommet 34 is further configured for being secured to a port 28 of the NIV patient interface 10. The scope guide tube 32 is thus flexibly held via the grommet 34 to the port of the NIV patient interface 10, enabling the distal end 46 of the exit guide portion 40 to be pivotally moved around and positioned proximate, but not in contact with, one of at least the nasal cavity or the mouth opening of the patient. As shown, the grommet 34 is secured to the port 28 via at least one of an elbow and an adapter, generally indicated by reference numeral 12. In addition, according to the embodiments of the present disclosure, the grommet 34 can be secured to the port 28 of the NIV patient interface via one of permanently secured or removably secured.

Figure 6:
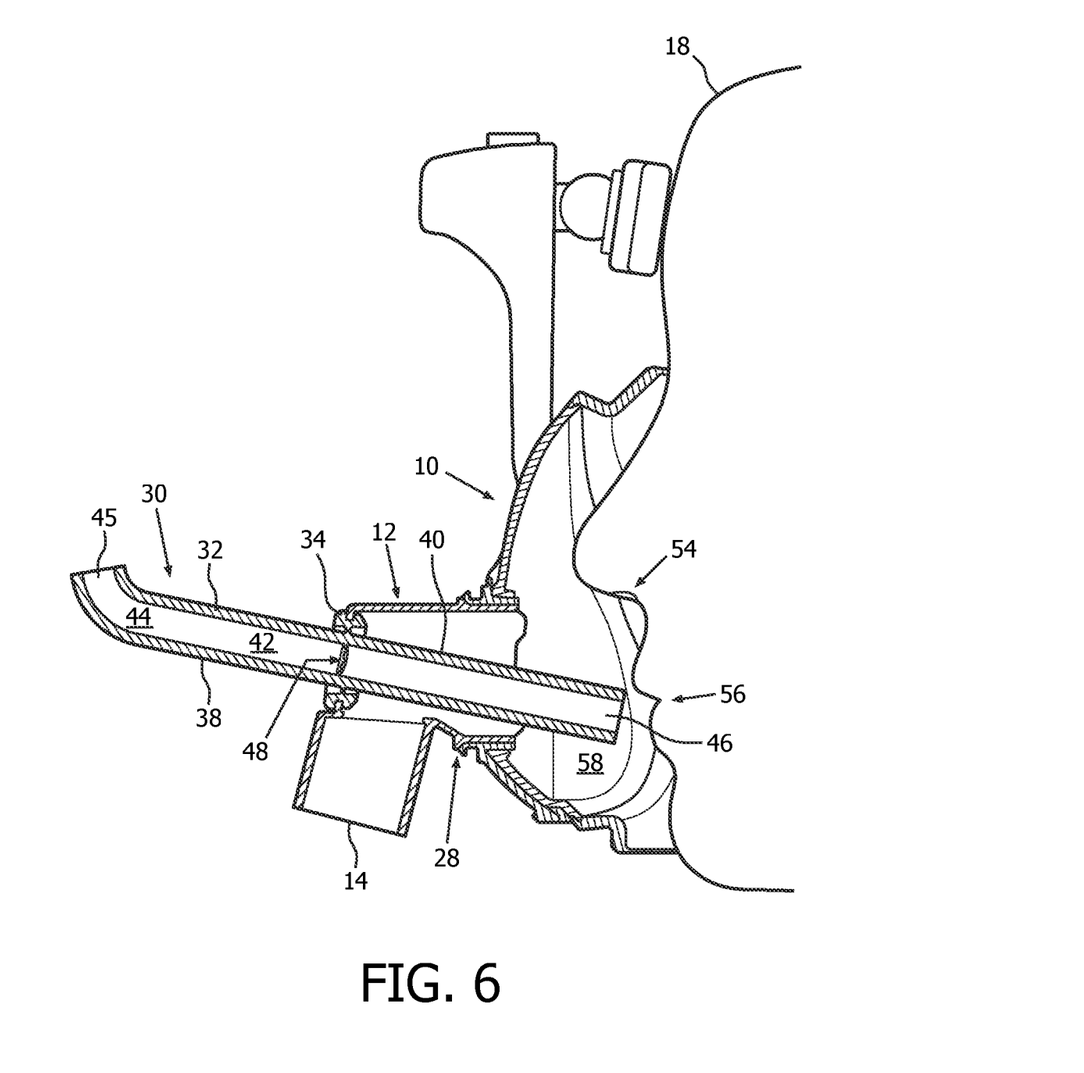
FIG. 6 is a sectional view along a length dimension of the bronchoscopy scope guide for a non-invasive ventilation (NIV) patient interface that comprises a reversible tube according to another embodiment of the present disclosure.

If removably secured, then the grommet 34 renders the bronchoscopy scope guide 30 removable for reuse thereof and/or for reuse of the NIV patient interface 10, as may be desired in a given situation. In addition, with an embodiment in which the grommet 34 is removably secured to the NIV patient interface 10, the scope guide tube 32 further comprises a reversible tube wherein the exit guide portion 40 can be used as the entrance guide portion 38, and vise versa. See for example, the illustration of FIG. 6 showing a sectional view along a length dimension of the bronchoscopy scope guide 30 for a non-invasive ventilation (NIV) patient interface 10 that comprises a reversible tube. In addition, a length of the entrance guide portion 38 shown in FIG. 6 has been illustrated as being longer than the entrance guide portion shown in FIG. 4, to convey that such length can be determined according to the particular requirements of a given bronchoscopy scope guide implementation.

In yet another embodiment, the grommet 34 can be permanently secured to the elbow/adapter/mask of the NIV patient interface 10, for example, via a permanent adhesive, via welding, or via any other suitable method. If the grommet 34 is permanently secured to the NIV patient interface 10, then the bronchoscopy scope guide 30 and the NIV patient interface 10 are part of each other. The bronchoscopy scope guide 30 would then further comprise an NIV patient interface. The NIV patient interface 10 can include one selected from the group consisting of a nasal mask, an oral-nasal face mask, and a helmet. In addition, the NIV patient interface 10 can comprise a non-invasive positive pressure ventilation (NPPV) mask.

In another embodiment, the scope guide tube 32 and grommet 34 form an integral component part. For example, the scope guide tube 32 and grommet 34 can comprise a hard durometer silicone or other semi-rigid material suitable for use in performing medical procedures. In another embodiment, the integral component part that comprises the scope guide tube 32 and grommet 34 further comprises the bronchoscopy scope seal 48. FIGS. 4 and 5 illustrate one example of the bronchoscopy scope guide 30 comprising a single integral component part that includes the scope guide tube 32, the grommet 34, and the bronchoscopy scope seal 48. In a further embodiment, the scope guide tube 32 could comprise a rigid material (e.g., thermoplastic) and the grommet 34 comprise a hard durometer silicone or other semi-rigid material suitable for use in performing medical procedures; however, in such an embodiment, the grommet 34 would still be flexibly coupled via the flexible intermediate region 50 to the scope guide tube 32, using a suitable attachment means. For example, the grommet could be mechanically attached using snaps or a "two shot" molding operation, where the rigid material is molded first and then placed into another mold, followed by molding of the flexible material directly onto the rigid material.

According to another embodiment, a method of guiding a bronchoscopy scope for a non-invasive ventilation (NIV) patient interface, comprises providing (i) a semi-rigid scope guide tube having a principal axis along a length dimension thereof, further having an entrance (input) guide portion and an exit (output) guide portion and (ii) a semi-rigid grommet. The semi-rigid grommet is disposed about an outer circumference of and flexibly coupled to the scope guide tube via a flexible intermediate region and located in a principal plane transverse to the principal axis of the scope guide tube, in-between the entrance and exit guide portions thereof. In addition, the method includes sealing between the scope guide tube and around a bronchoscopy scope, via a bronchoscopy scope seal coupled to the scope guide tube, in response to the bronchoscopy scope being inserted through the scope guide tube, further enabling maintaining of a positive pressure within the patient interface during usage of the patient interface for non-invasive ventilation. Furthermore, the method includes pivotally manipulating the scope guide tube about the flexible coupling of the grommet for positioning a distal end of the exit guide portion of the scope guide tube proximate, but not in contact with, one of a nasal cavity or mouth opening of a patient for assisted guidance control of the bronchoscopy scope within an interior region of the patient interface that extends from at least an interior surface of the patient interface to the patient's face, and for preventing undesirable bending or looping of the bronchoscopy scope within the interior region of the patient interface during insertion of the bronchoscopy scope into the nasal cavity or mouth opening and associated airway of the patient in performance of a bronchoscopy procedure.

In a further embodiment, the method also comprises securing the grommet to the NIV patient interface via at least one of directly to a port of the NIV patient interface, indirectly via an elbow coupled to the port, and indirectly via an adapter coupled to the port, wherein the scope guide tube is flexibly held via the grommet to the port of the NIV patient interface, enabling the distal end of the exit guide portion to be pivotally moved around and positioned proximate, but not in contact with, one of at least the nasal cavity or the mouth opening of the patient. In addition, the method includes wherein the grommet is secured to the port of the NIV patient interface via one of permanently secured or removably secured. In the instance of the grommet being removably secured to the NIV patient interface, the scope guide tube further comprises a reversible tube in which the exit guide portion can be used as the entrance guide portion and vise versa.

Accordingly, the scope guide tube is advantageous for guiding a highly flexible bronchoscopy scope through the NIV patient interface, across a ventilation region within the NIV patient interface, to a correct location for entry into a patient airway (nasal or mouth opening) without the highly flexible bronchoscopy scope tube bending or looping within the ventilation region inside the NIV patient interface.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in patient interface devices for continuous positive airway pressure (CPAP), NIV, NPPV applications, while performing a bronchoscopy procedure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A bronchoscopy scope guide for a non-invasive ventilation (NIV) patient interface, comprising:
    a scope guide tube having a principal axis along a length dimension thereof, further having an entrance guide portion and an exit guide portion, wherein the scope guide tube comprises a semi-rigid tube made from a material having Shore A hardness of 60-100;
    a bronchoscopy scope seal coupled to the scope guide tube for sealing between the scope guide tube and around a bronchoscopy scope, wherein the bronchoscopy scope seal is configured to maintain a positive pressure within the patient interface during usage of the patient interface for non-invasive ventilation when the bronchoscopy scope is inserted through the scope guide tube and when the bronchoscopy scope is not inserted through the scope guide tube; and
    a semi-rigid grommet being disposed about an outer circumference of and flexibly coupled permanently, via a flexible intermediate region of the semi-rigid grommet, to the scope guide tube, in-between the entrance and exit guide portions thereof, and located in a principal plane transverse to the principal axis of the scope guide tube, the semi-rigid grommet being made from a material having Shore A hardness of 60-100, wherein the scope guide tube is pivotally manipulate-able about the flexible intermediate region of the semi-rigid grommet for positioning a distal end of the exit guide portion of the scope guide tube proximate, but not in contact with, one of a nasal cavity or mouth opening of a patient for assisted guidance control of the bronchoscopy scope within an interior region of the patient interface that is configured to extend from at least an interior surface of the patient interface to the patient's face, and for preventing undesirable bending or looping of the bronchoscopy scope within the interior region of the patient interface during insertion of the bronchoscopy scope into the nasal cavity or mouth opening and associated airway of the patient in performance of a bronchoscopy procedure.

2. The bronchoscopy scope guide according to claim 1, wherein a length of the exit guide portion of the scope guide tube comprises a length sufficient to enable a desired pivotal movement of the exit guide portion within the interior region of the patient interface, but not a length insertable into the nasal or mouth opening and associated airway of the patient.

3. The bronchoscopy scope guide according to claim 1, wherein the semi-rigid grommet is further configured for being secured to a port of the NIV patient interface, wherein the scope guide tube is flexibly held via the semi-rigid grommet to the port of the NIV patient interface, enabling the distal end of the exit guide portion to be pivotally moved around and positioned proximate, but not in contact with, one of at least the nasal cavity or the mouth opening of the patient.

4. The bronchoscopy scope guide according to claim 3, further wherein the semi-rigid grommet is secured to the port via at least one of an elbow and an adapter.

5. The bronchoscopy scope guide according to claim 3, wherein the semi-rigid grommet is permanently secured to the port of the NIV patient interface.

6. The bronchoscopy scope guide according to claim 3 wherein the grommet is removably secured to the port of the NIV patient interface.

7. The bronchoscopy scope guide according to claim 1, wherein the scope guide tube and semi-rigid grommet form an integral component part.

8. The bronchoscopy scope guide according to claim 7, wherein the integral component part further comprises the bronchoscopy scope seal.

9. The bronchoscopy scope guide according to claim 1, wherein the scope guide tube and semi-rigid grommet comprise a hard durometer silicone having a Shore A hardness of 60-80.

10. The bronchoscopy scope guide according to claim 1, further comprising:
    an NIV patient interface, wherein the NIV patient interface comprises one selected from the group consisting of a nasal mask, an oral-nasal face mask, and a helmet.

11. The bronchoscopy scope guide according to claim 10, further wherein the NIV patient interface comprises a non-invasive positive pressure ventilation (NPPV) mask.

12. The bronchoscopy scope guide according to claim 1, wherein the semi-rigid grommet is removably secured to the NIV patient interface such that the scope guide tube is reversible.

13. The bronchoscopy scope guide according to claim 1, wherein the entrance guide portion comprises a straight section along the principal axis of the scope guide tube and the exit guide portion comprises both a straight section along the principal axis and a curved section curving away from the principal axis of the scope guide tube.

14. The bronchoscopy scope guide according to claim 13, further wherein the curved section of exit guide portion is located at a distal end thereof.

15. The bronchoscopy scope guide according to claim 1, wherein the entrance guide portion is straight along the principal axis and the exit guide portion includes a section that curves away from the principal axis.

16. The bronchoscopy scope guide according to claim 1, wherein the bronchoscopy scope seal couples to the scope guide tube at a position within the entrance guide portion or the exit guide portion, or at an intersection of the entrance guide portion and the exit guide portion.

17. The bronchoscopy scope guide according to claim 16, wherein the bronchoscopy scope seal is located within the scope guide tube at a location of the semi-rigid grommet.

18. A method of guiding a bronchoscopy scope for a non-invasive ventilation (NIV) patient interface, comprising:
providing (i) a scope guide tube having a principal axis along a length dimension thereof, further having an entrance guide portion and an exit guide portion, wherein the scope guide tube comprises semi-rigid tube made from a material having Shore A hardness of 60-120 and (ii) a semi-rigid grommet being disposed about an outer circumference of and flexibly coupled permanently, via a flexible intermediate region of the semi-rigid grommet, to the scope guide tube, in-between the entrance and exit guide portions thereof, and located in a principal plane transverse to the principal axis of the scope guide tube, the semi-rigid grommet being made from a material having Shore A hardness of 60-100;
sealing between the scope guide tube and around a bronchoscopy scope, via a bronchoscopy scope seal coupled to the scope guide tube, wherein the bronchoscopy scope seal is configured to maintain a positive pressure within the patient interface during usage of the patient interface for non-invasive ventilation when the bronchoscopy scope is inserted through the scope guide tube and when the bronchoscopy scope is not inserted through the scope guide tube; and
pivotally manipulating the scope guide tube about the flexible intermediate region of the semi-rigid grommet for positioning a distal end of the exit guide portion of the scope guide tube proximate, but not in contact with, one of a nasal cavity or mouth opening of a patient for assisted guidance control of the bronchoscopy scope within an interior region of the patient interface that is configured to extend from at least an interior surface of the patient interface to the patient's face, and for guiding the bronchoscopy scope across the interior region of the patient interface, to a correct location for entry into a patient airway without the bronchoscopy scope bending or looping within the interior region.

19. The method according to claim 18, further comprising:
securing the semi-rigid grommet to the NIV patient interface via at least one of directly to a port of the NIV patient interface, indirectly via an elbow coupled to the port, and indirectly via an adapter coupled to the port, wherein the scope guide tube is flexibly held via the semi-rigid grommet to the port of the NIV patient interface, enabling the distal end of the exit guide portion to be pivotally moved around and positioned proximate, but not in contact with, one of at least the nasal cavity or the mouth opening of the patient.

20. The method according to claim 18, wherein the semi-rigid grommet is permanently secured to the port of the NIV patient interface.

21. The method according to claim 18, wherein the semi-rigid grommet is removably secured to the NIV patient interface such that the scope guide tube is reversible.

22. The bronchoscopy scope guide according to claim 18 wherein the grommet is removably secured to the port of the NIV patient interface.

* * * * *